United States Patent [19]

Warden

[11] Patent Number: 5,204,892
[45] Date of Patent: Apr. 20, 1993

[54] PRIMARY RADIATION DIAPHRAGM FOR X-RAY TUBE

[75] Inventor: Hans-Erik Warden, Upplands Vaesby, Sweden

[73] Assignee: Siemens Aktiengesellschaft, Munich

[21] Appl. No.: 789,239

[22] Filed: Nov. 6, 1991

[30] Foreign Application Priority Data

Nov. 14, 1990 [SE] Sweden ............................ 90036385

[51] Int. Cl.⁵ ........................................ G21K 1/04
[52] U.S. Cl. .................................. 378/152; 378/150
[58] Field of Search .................... 378/150, 152, 153

[56] References Cited

U.S. PATENT DOCUMENTS

| | | | |
|---|---|---|---|
| 1,909,118 | 5/1933 | Raab . | |
| 3,048,700 | 8/1962 | Koerner et al. | 378/152 |
| 4,158,779 | 6/1979 | Rommel et al. | 378/152 |
| 4,943,990 | 7/1990 | Schär | 378/150 |

FOREIGN PATENT DOCUMENTS

| | | |
|---|---|---|
| 1441312 | 10/1968 | Fed. Rep. of Germany . |
| 2035110 | 2/1972 | Fed. Rep. of Germany ...... 378/150 |
| 635489 | 3/1928 | France . |
| 832373 | 4/1960 | United Kingdom . |

OTHER PUBLICATIONS

Siemens Brochure for RUREK X-Ray Collimator.

*Primary Examiner*—Craig E. Church
*Attorney, Agent, or Firm*—Hill, Steadman & Simpson

[57] ABSTRACT

A primary radiation diaphragm for an x-ray tube has a first group of diaphragm plates disposed proximate the focus of the x-ray tube, and a second group of diaphragm plates disposed distal of the focus. Each group of diaphragm plates consists of two diaphragm plate pairs, the plate pairs in each group forming a parallelogram. The diaphragm plates in each plate pair are adjustable together, with reference to the longitudinal axis of the overall radiation diaphragm structure by a control element, so that a ray pyramid having a desired size is formed. A single first shaft is used as a control element for simultaneously adjusting the diaphragm plates in one plate pair in the first group and one plate in the second group, the first shaft engaging each of the plates in these respective plate pairs for that purpose. A second single shaft engages the diaphragm plates in the other plate pair in the first group and the other plate pair in the second group, for simultaneously adjusting those plate pairs.

2 Claims, 3 Drawing Sheets

PRIMARY RADIATION DIAPHRAGM FOR X-RAY TUBE

BACKGROUND OF THE INVENTION

1. Field of the Invention

The present invention is directed to a primary radiation diaphragm for an x-ray tube of the type having two sets of diaphragm plates disposed parallel to each other, with one set being proximate the focus of the x-ray tube and the other set being distal of the focus, so that a ray pyramid is formed by adjusting the respective sets of plates.

2. Description of the Prior Art

A primary radiation diaphragm for an x-ray tube is disclosed in German OS 1 441 312 wherein a first group of diaphragm plates is formed by two diaphragm plate pairs disposed relative to each other to form an opening for the passage of radiation proximate the focus of the x-ray tube. A second group of two diaphragm plate pairs is disposed distal of the focus and parallel to the plates in the first group, the plate pairs in the second group also forming an opening for radiation passage. The diaphragm plates in each diaphragm plate pair are adjustable in common with reference to the longitudinal axis of the overall radiation diaphragm structure. The diaphragm plate pairs in the first group and the diaphragm plate pairs in the second group are symmetrically disposed relative to the longitudinal axis with the same orientation, so that a ray pyramid having a desired size is formed, the tip of the pyramid being coincident with the x-ray tube focus.

In this known structure, setting or adjustment of the diaphragm plates is undertaken by means of drive rollers and drive belts, so that the two plates in each plate pair are adjusted in common. The use of such drive rollers and drive belts makes the structure of this known primary radiation diaphragm relatively complicated. As a result of the use of a belt drive, moreover, a certain amount of play can arise upon the displacement of the diaphragm plates, which degrades the precision with which the overall radiation diaphragm structure can be set.

Another primary radiation diaphragm of the type having diaphragm plates arranged in parallel, spaced planes is commercially available under the designation "Rurek X-ray Collimator." This type of diaphragm is a so-called multi-leaf collimator with the diaphragm plates in one of the planes being arranged to form an iris diaphragm. The adjustment of the diaphragm plates in the respective diaphragm planes is undertaken separately.

SUMMARY OF THE INVENTION

It is an object of the present invention to provide a primary radiation diaphragm of the type described above which is simple in structure but nonetheless permits the plates to be set with high precision.

The above object is achieved in a primary radiation diaphragm wherein a single first shaft directly engages a diaphragm plate pair in the first group and a diaphragm plate pair in the second group so that those two plate pairs in the respective first and second groups are adjusted in common and simultaneously by this first shaft. A second single shaft directly engages the other diaphragm plate pair in the first group and the other diaphragm plate pair in the second group, and simultaneously adjusts those two plate pairs in the respective first and second groups. An very simple primary radiation diaphragm structure is thus obtained, which nonetheless permits the plates to be adjusted with high precision due to the direct connection of the first and second shafts with the respective diaphragm plate pairs. The structure of the primary radiation diaphragm disclosed herein also permits the overall structure to be supplemented in a simple manner with further diaphragm plates, as may be needed under some circumstances, which can be attached between the first and second groups of diaphragm plate pairs. Such further plate pairs can then also be simultaneously adjusted by the respective first and second shafts, so that all of the diaphragm plate pairs can be adjusted in common by means of no more than two control shafts. A more effective gating of the radiation is made possible by the use of such further diaphragm plates, if necessary.

In one embodiment of the invention, the diaphragm plates in each diaphragm plate pair are respective portions of a parallelogram arm system, and each diaphragm plate in the diaphragm plate pairs have a toothed portion directly attached to an arm in the parallelogram system, the toothed segment directly engaging a toothed wheel attached to the control shaft for that diaphragm plate pair. Exact transmission of the motion of the toothed wheel is thus transferred from the shaft to the toothed portion, thereby permitting precise adjustment of each diaphragm plate pair.

In a further version of the above embodiment, the toothed portion itself forms an arm in parallelogram system. This permits the parallelogram arm system to be made small, so that the diaphragm plates can also be made correspondingly small. A diaphragm plate pair constructed in accordance with this version is thus suitable for placement in the proximity of the focus of the x-ray tube, because it can easily form the top of the ray pyramid.

The toothed wheels are preferably rigidly attached to the respective control shafts.

As noted above, the first group of diaphragm plate pairs is preferably smaller in size than the second group of diaphragm plate pairs, so that the overall structure of the primary radiation diaphragm is in the shape of a truncated cone. As a result, the overall primary radiation diaphragm can be made relatively small and lightweight, which is advantageous particularly for use in combination with a single tank radiator for a mobile x-ray unit, because the single tank radiator must be maintained as small and lightweight as possible.

In a further embodiment of the invention, the teeth of the toothed portions are shaped (angled) to correspond to the angles of the control shafts in relationship to the longitudinal axis of the diaphragm. Because the first group of diaphragm plates is smaller than the second group, the control shafts will be disposed at an angle relative to the longitudinal axis. By similarly angling the teeth of the toothed portions of the plates, the toothed wheels can be attached to the respective control shafts in a normal (i.e., non-angled) manner, regardless of the angles of the shafts.

In a further embodiment of the invention, the toothed portions of the diaphragm plates, which engage the toothed wheels of the respective control shafts, are mounted to as to be rotatable around an axis, so that rotation of the control shaft causes rotation of the respective diaphragm plate around that axis. An increase in the adjustment precision over known radiation diaphragms can be achieved even if only one pair of diaphragm plates in each of the first and second groups are simultaneously adjustably by a single control shaft. The remaining pairs of diaphragm plates in each of the first and second groups can be adjusted using a second, common control shaft, as described above, or may be adjustable by some other means.

DESCRIPTION OF THE PREFERRED EMBODIMENTS

Figure 1:
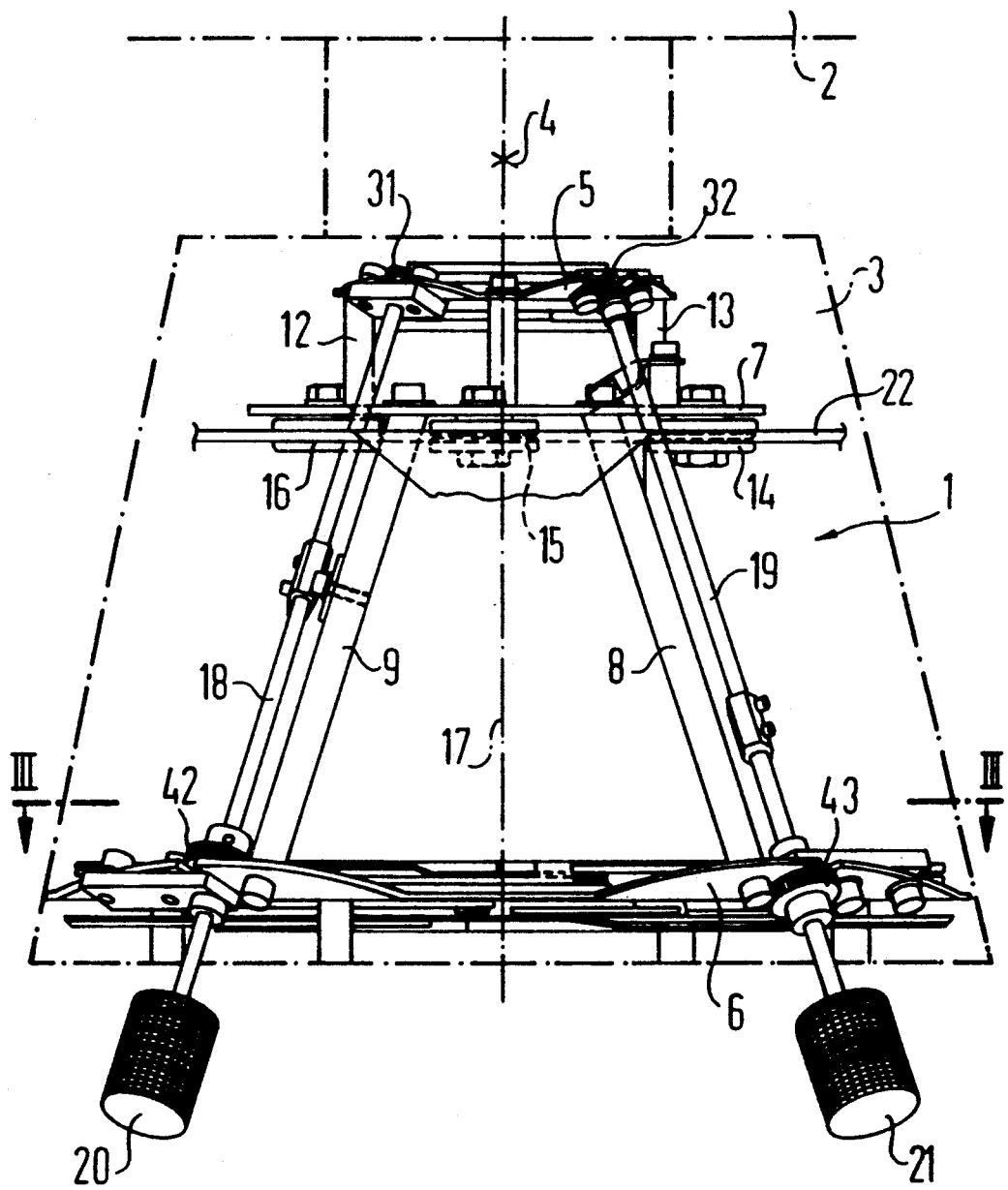
FIG. 1 is a side view of a primary radiation diaphragm constructed in accordance with the principles of the present invention.

A primary radiation diaphragm 1 constructed in accordance with the principles of the present invention is shown in FIG. 1, for use with a schematically-indicated x-ray tube 2. The x-ray tube 2 is connected to a schematically-indicated housing 3 of the primary radiation diaphragm 1. The primary radiation diaphragm 1 is a so-called "depth diaphragm" or multi-leaf collimator, having two diaphragm planes with a first group of two diaphragm plate pairs disposed perpendicularly relative to each other in one plane close to the focus 4 of the x-ray tube, mounted on a flange 5. Further structural details of these diaphragm plate pairs are described below in connection with FIG. 2. A second group of two diaphragm plate pairs, also arranged perpendicularly relative to each other, is disposed a larger distance from the focus 4, attached to a flange 6. Structural details of the second group of diaphragm plate pairs are set forth below in connection with FIG. 3.

As can be seen in FIG. 1, the flange 5 to which the first group of diaphragm plate pairs is mounted is smaller than the flange 6 to which the second group of diaphragm plate pairs is mounted, so that the primary radiation diaphragm 1 has the shape of a truncated cone. A plate 7 is attached between the flanges 5 and 6. Spacer elements 8, 9, 10 and 11 are disposed between the plate 7 and the flange 6, with only the spacer elements 8 and 9 being visible in FIG. 1. Further spacer elements 12 and 13 are attached between the plate 7 and the flange 5. The plate 7 carries rollers 14, 15 and 16 each having a channel which receives a guide plate 22 attached to the interior of the housing 3. This permits the entire primary radiation diaphragm 1 to be rotated around its longitudinal axis 17.

Within the first group of diaphragm plate pairs mounted at the flange 5, one diaphragm plate pair is mounted to the upper side of the flange 5 and the other diaphragm plate pair is mounted to the lower side of the flange 5. Similarly, in the second group of diaphragm plate pairs, one diaphragm plate pair is mounted at the upper side and the flange 6, and the other diaphragm plate pair is mounted at the lower side of the flange 6. The diaphragm plate pairs which are respectively mounted at the upper sides of the flanges 5 and 6 are connected to each other by a shaft 18 via control elements (set forth in detail below) formed by toothed wheels and toothed segments. The respective diaphragm plate pairs which are mounted at the lower sides of the flanges 5 and 6 are connected to each other by a shaft 19 via similar control elements (also set forth in detail below). The shaft 18 has a knob 20 and the shaft 19 has a knob 21. By turning the knobs 20 and 21, the respective shafts 18 and 19 can be rotated around their respective longitudinal axes, so that the diaphragm plate pairs respectively engaging the shafts 18 and 19 can be to a desired position.

Figure 2:
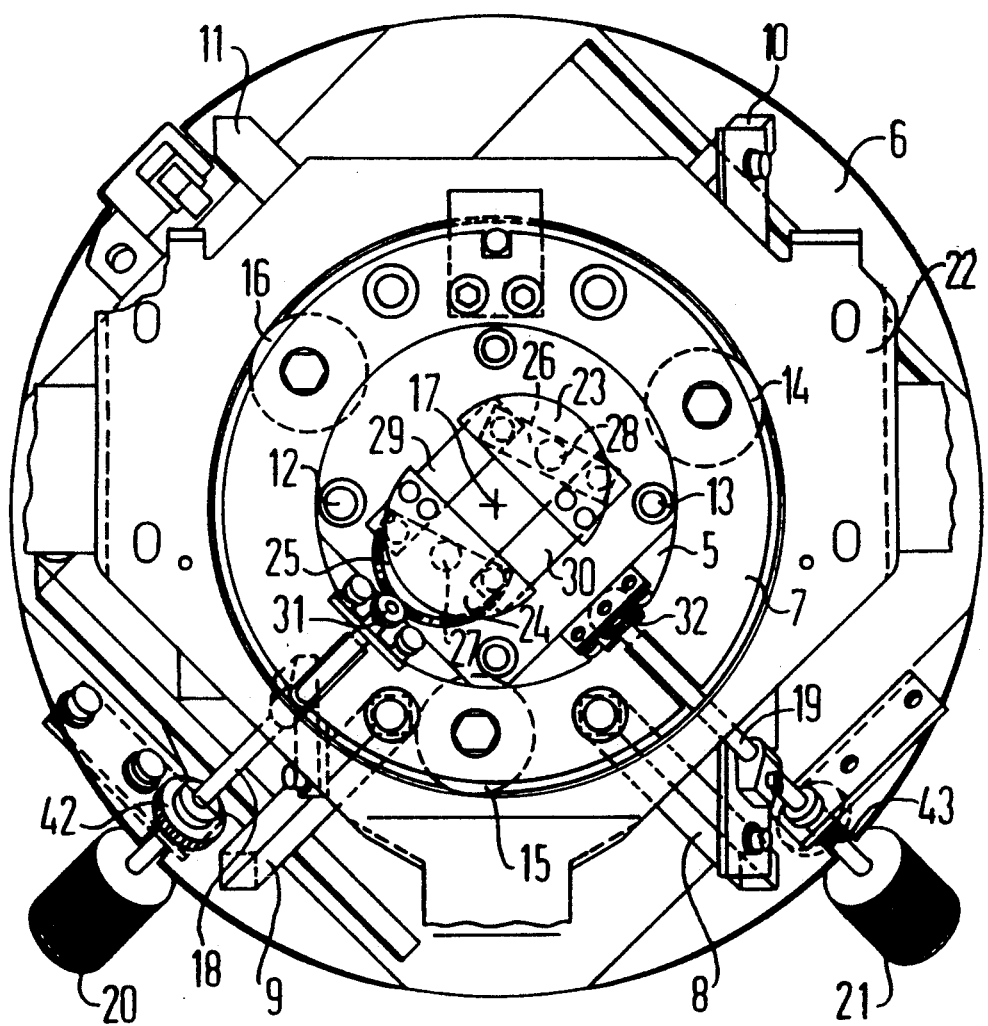
FIG. 2 is a plan view of a primary radiation diaphragm constructed in accordance with the principles of the present invention shown in FIG. 1.

Diaphragm plates 23 and 24 which are mounted at the upper side of the flange 5 are shown in FIG. 2. As can be seen in FIG. 2, the diaphragm plates 23 and 24 are components of a parallelogram arm system having transverse arms 25 and 26 which are respectively rotatable around axes 27 and 28. The parallelogram arm system also includes longitudinal arms 29 and 30 which are respectively rotatable around the transverse arms 25 and 26. The diaphragm plate 24 is attached to the arm 29, and the diaphragm plate 23 is attached to the arm 30. In the embodiment of the parallelogram arm system shown in FIG. 2, the transverse arm 25 is a toothed segment. The toothed segment transverse arm 25 is rotatable around the axis 27 by means of engagement with a toothed wheel 31, which is secured to the shaft 18 and presses against the toothed segment transverse arm 25. By turning the toothed segment transverse arm 25 by means of the toothed wheel 31, the diaphragm plates 23 and 24 are displaced relative to each other until a desired position is achieved. A similar diaphragm plate pair, oriented perpendicularly relative to the diaphragm plates 23 and 24, is mounted at the underside of the flange 5, and therefore cannot be seen in FIG. 2. The plate pair mounted at the underside of the flange 5, however, does not differ in structure from the above-described plates pair 23 and 24, except that the toothed segment for the control of the plates mounted at the underside of the flange 5 is accomplished by means of a toothed wheel 32 secured to the shaft 19. By turning the toothed segment with the toothed wheel 32 by rotating the shaft 19 with the knob 21, the diaphragm plates mounted under the flange 5 are also displaced relative to each other to a desired position.

Figure 3:
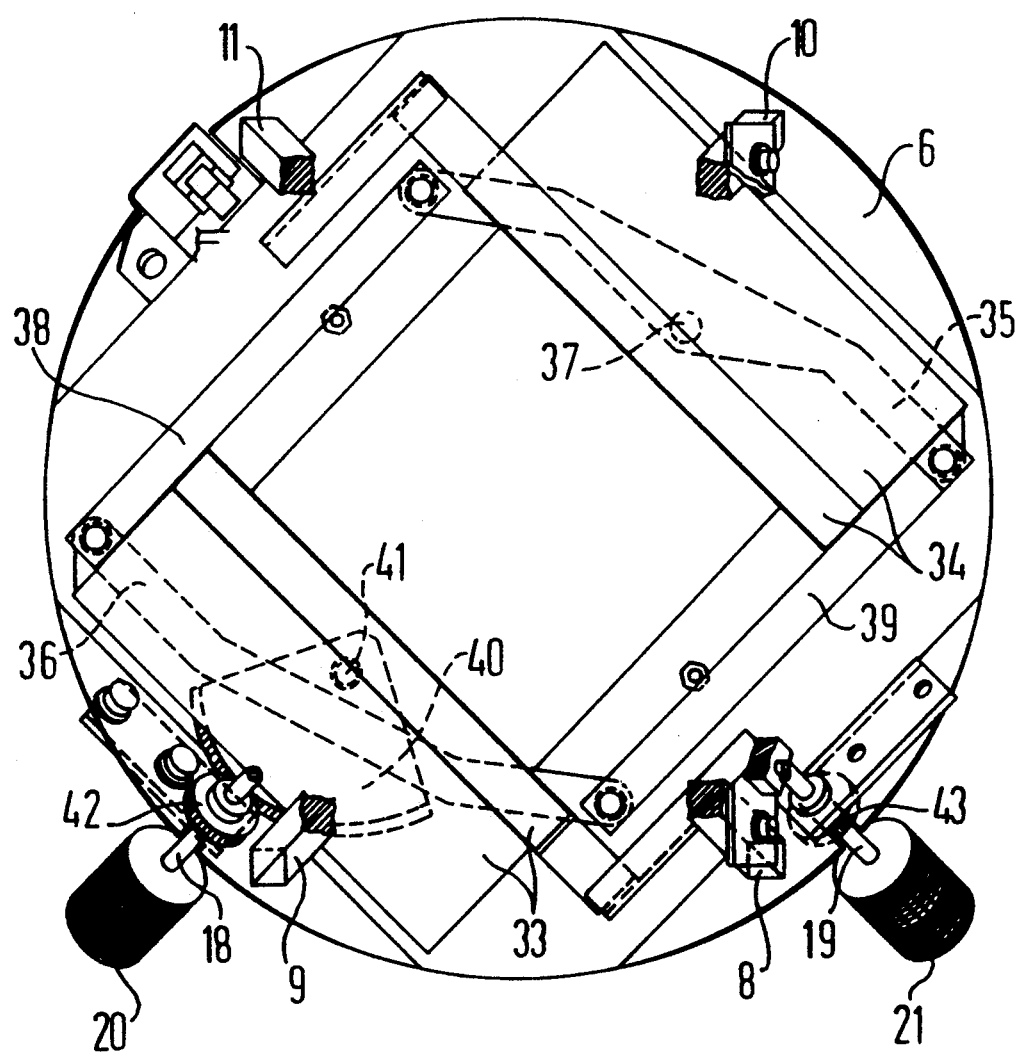
FIG. 3 is a sectional view of the primary radiation diaphragm constructed in accordance with the principles of the present invention, taken along line III—III of FIG. 1.

Diaphragm plates 33 and 34 mounted at the upper side of the shoulder 6 are shown in FIG. 3. The diaphragm plates 33 and 34 are part of a parallelogram arm system including transverse arms 35 and 36, the transverse arm 35 being rotatable around a shaft 37. The parallelogram arm system also includes longitudinal arms 38 and 39 which are respectively rotatable around the transverse arms 35 and 36. The diaphragm plate 33 is attached to the arm 38 and the diaphragm plate 34 is attached to the arm 39. A toothed segment 40 is directly attached to the transverse arm 36, and is mounted so as to be rotatable around an axis 41. The toothed segment 40, and thus the arm 36 as well, can be rotated around the axis 41 by means of the toothed wheel 42, which is secured to the shaft 18 and engages the toothed segment. By turning the toothed segment 40, the diaphragm plates 33 and 34 are displaced relative to each other to a desired position. A further diaphragm plate pair is mounted at the underside of the flange 6 oriented perpendicularly relative to the plates 33 and 34, and therefore cannot be seen in FIG. 3. The diaphragm plate pair mounted at the underside of the flange 6 does not differ in structure from the diaphragm plates 33 and 34, except that the toothed segment for control of those diaphragm plates is turned by means of a toothed wheel 43 attached to the shaft 19. By turning the toothed segment, by rotation of the toothed wheel 43 by rotating the knob 21, the diaphragm plates mounted at the underside of the flange 6 are displaced relative to other to a desired position.

The teeth of all the toothed segments are shaped to correspond to the angles of the shafts 18 and 19 with respect to the longitudinal axis 17 of the primary radiation diaphragm. The teeth of the toothed wheels can thus be straight, i.e., parallel to the shafts 18 and 19, and the toothed wheels can be attached to the respective shafts 18 and 19 so as to extend radially perpendicularly therefrom.

In order to bring the plate pair consisting of plates 23 and 24 at the upper side of the flange 5 and the plate pair consisting of the plates 33 and 34 at the upper side of the flange 6 to a desired position, the knob 20 is rotated until these diaphragm plates have reached the desired position, both pairs being displaced in common and simultaneously. In the same manner, the respective diaphragm plate pairs mounted under the flanges 5 and, 6 are displaced relative to the diaphragm plates 23 and 24, and the diaphragm plates 33 and 34, by rotating the knob 21. As stated above, the respective diaphragm plate pairs mounted at the upper sides of the flanges 5 and 6 are oriented perpendicularly relative to the respective diaphragm plate pairs mounted under the flanges 5 and 6.

The relationship between the toothed wheels and the toothed segments of the respective pairs of diaphragm plates mounted above and below the flanges 5 and 6 are selected so that the diaphragm plate pairs are adjusted synchronously in a simple manner so that a ray pyramid having the desired size can be formed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A primary radiation diaphragm for an x-ray tube comprising:

a first group of first and second perpendicularly disposed pairs of diaphragm plates mounted proximate a focus of an x-ray tube;

a second group of third and fourth perpendicularly disposed pairs of diaphragm plates mounted distally of said focus;

each of said first, second, third and fourth pairs of diaphragm plates having a respective control means associated therewith for displacing the diaphragm plates in the pair;

a first rotatable shaft mounted to engage said control means of said first and third pairs of diaphragm plates causing simultaneous displacement of said diaphragm plates in said first and third pairs relative to a longitudinal axis extending substantially perpendicularly between said first and second groups;

a second rotatable shaft mounted to engage said control means of said second and fourth pairs of diaphragm plates causing simultaneous displacement of said diaphragm plates in said second and fourth pairs relative to said longitudinal axis;

said first, second, third and fourth pairs of diaphragm plates respectively forming parts of first, second, third and fourth parallelogram arm systems, wherein said control means for each of said first second, third and fourth pairs of diaphragm plates is a respective toothed segment attached to an arm in said respective first, second, third and fourth parallelogram arm systems, and wherein each control means further includes a toothed wheel rigidly attached to a respective rotatable shaft and engaged with said toothed segment;

said first group of diaphragm plate pairs being smaller in size than said second group of diaphragm plate pairs so that said primary radiation diaphragm has the shape of a truncated cone, with said first and second shafts being disposed at a non-parallel angle to said longitudinal axis; and said first group of pairs of diaphragm plates defining a first opening for passage of radiation from said focus of said x-ray tube and said second group of pairs of diaphragm plates defining a second opening for passage of said radiation, said first opening being smaller than said second opening so that a radiation pyramid, having tip coinciding with said focus, of desired shape is formed by rotating said first and second shafts.

2. A primary radiation diaphragm as claimed in claim 1 wherein said toothed segments have teeth disposed at said non-parallel angle of said shafts relative to said longitudinal axis.

* * * * *